US007979288B2

(12) United States Patent
Wilkinson et al.

(10) Patent No.: US 7,979,288 B2
(45) Date of Patent: Jul. 12, 2011

(54) AUTOMATED INTERPRETATION OF MEDICAL PRESCRIPTION TEXT

(75) Inventors: Jeff Wilkinson, San Antonio, TX (US); William Arensman, San Antonio, TX (US); Nathan Price, San Antonio, TX (US); John Madrid, San Antonio, TX (US); Keith Pickens, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 683 days.

(21) Appl. No.: 11/871,909

(22) Filed: Oct. 12, 2007

(65) Prior Publication Data

US 2009/0099870 A1   Apr. 16, 2009

(51) Int. Cl.
*G06F 19/00* (2011.01)
(52) U.S. Cl. .................. 705/3; 705/2; 704/10; 715/205; 715/743; 600/300; 600/509
(58) Field of Classification Search .................. 705/2, 3; 704/10; 715/205, 743; 1/1; 600/300
See application file for complete search history.

(56) References Cited

U.S. PATENT DOCUMENTS

| | | | | | |
|---|---|---|---|---|---|
| 5,737,539 | A | * | 4/1998 | Edelson et al. | 705/3 |
| 5,758,095 | A | * | 5/1998 | Albaum et al. | 705/2 |
| 5,823,948 | A | * | 10/1998 | Ross et al. | 600/300 |
| 5,832,450 | A | * | 11/1998 | Myers et al. | 705/3 |
| 6,226,620 | B1 | * | 5/2001 | Oon | 705/2 |
| 7,072,840 | B1 | | 7/2006 | Mayoud | |
| 7,096,212 | B2 | * | 8/2006 | Tribble et al. | 1/1 |
| 7,225,408 | B2 | * | 5/2007 | O'Rourke | 715/743 |
| 7,657,521 | B2 | * | 2/2010 | Masarie et al. | 704/10 |
| 2002/0161795 | A1 | * | 10/2002 | O'Rourke | 707/500 |
| 2003/0097368 | A1 | * | 5/2003 | Tribble et al. | 707/102 |
| 2004/0153336 | A1 | * | 8/2004 | Virdee et al. | 705/2 |
| 2004/0205042 | A1 | * | 10/2004 | Ritter et al. | 707/2 |

OTHER PUBLICATIONS google patent search history.*
Dialog search results.*
Dialog search results_2.*
"Business Rule," available at http://en.wikipedia.org/wiki/Business_rule; retrieved on Oct. 3, 2007.
"Computer Physician Order Entry," available at http://en.wikipedia.org/wiki/Computer_physician_order_entry; retrieved on Oct. 3, 2007.
"Context-free Grammar," available at http://en.wikipedia.org/wiki/Context-free_Grammar; retrieved on Oct. 3, 2007.
"Graphical User Interface" available at http://en.wikipedia.org/wiki/Graphical_User_Interface; retrieved on Oct. 3, 2007.
"Medical Prescription," available at http://en.wikipedia.org/wiki/Medical_prescription; retrieved on Oct. 8, 2007.
"Natural Language Processing," available at http://en.wikipedia.org/wiki/Natural_Language_Processing; retrieved on Oct. 8, 2007.

(Continued)

*Primary Examiner* — Dilek B Cobanoglu
(74) *Attorney, Agent, or Firm* — Grossman, Tucker et al.

(57) ABSTRACT

The present disclosure relates to a device, system and method of automated interpretation of medical prescription text. Prescription text may be entered into a user interface that may be analogous to a paper prescription entry such as manually written text. The system may then provide parsing, prompts and/or hints along with validity feedback as the prescription information is entered by the user.

15 Claims, 10 Drawing Sheets

OTHER PUBLICATIONS

"Parsing," available at http://en.wikipedia.org/wiki/Parsing; retrieved on Oct. 3, 2007.

"Pattern Recognition," available at http://en.wikipedia.org/wiki/Pattern_Recognition; retrieved on Oct. 3, 2007.

"Standard Generalized Markup Language," available at http://en.wikipedia.org/wiki/Standard_Generalized_Markup_Language; retrieved on Oct. 3, 2007.

"XML," available at http://en.wikipedia.org/wiki/XML; retrieved on Oct. 3, 2007.

Definition of "Parse," available at http://foldoc.org/?query=parse; retrieved on Oct. 3, 2007.

Arensman, et al. "Automated Interpretation of Medical Prescription Text," available at http://www.swri.org/3pubs/ IRD2006/Synopses/109642.htm; retrieved on Oct. 4, 2007.

* cited by examiner

FIG. 2

```
<patterns>
<pattern numUses="3">
<term type="Medication Name" />
<term type="Strength" />
<term type="Dose Form" />
</pattern>
<pattern numUses="2">
<term type="Strength" />
<term type="Dose Form" />
<term type="Medication Name" />
</pattern>
<patterns>
```

| Edit | Id | Typeid | String | Username | Numuses |
|------|------|--------|----------------------|----------|---------|
| 🖉 | 1421 | 4 | BID | nprice | 88 |
| 🖉 | 1422 | 7 | X 10 DAYS | nprice | 69 |
| 🖉 | 1423 | 6 | #30 | nprice | 63 |
| 🖉 | 1427 | 5 | PO | nprice | 63 |
| 🖉 | 1419 | 1 | TYLENOL EXTRA STRENGTH | nprice | 65 |
| 🖉 | 1420 | 2 | 100MG | nprice | 53 |
| 🖉 | 1428 | 2 | 200MG | nprice | 1 |
| 🖉 | 1429 | 2 | 500MG | nprice | 2 |
| 🖉 | 1430 | 1 | IBUPROFEN | nprice | 3 |
| 🖉 | 1520 | 1 | ANCEF | nprice | 1 |
| 🖉 | 1503 | 1 | PREDNISONE | nprice | 2 |
| 🖉 | 1509 | 1 | POLYTRIM | nprice | 1 |
| 🖉 | 1488 | 1 | RITALIN | nprice | 1 |
| 🖉 | 1492 | 1 | ROCEPHEN | nprice | 2 |
| 🖉 | 1436 | 2 | 100ML | nprice | 9 |

FIG. 9

AUTOMATED INTERPRETATION OF MEDICAL PRESCRIPTION TEXT

FIELD OF INVENTION

The present disclosure relates to a device, system and method of automated interpretation of medical prescription text. In particular, prescription text may be entered into a user interface that may be analogous to a paper prescription entry such as manually written text and the system may then provide parsing, prompts and/or hints along with validity feedback as the prescription information is entered by the user.

BACKGROUND

Computerized physician order entry may be understood as a process of electronic entry of physician instructions for treatment of patients. Orders may include prescriptions, laboratory screenings, x-rays or other examinations, that may be ordered by a physician or other health care provider communicated over a network to those who may carry out or fulfill orders. For example, an order may include a prescription for a drug, which is communicated to a pharmacy. The pharmacy may then fill the prescription and provide the prescription to the patient or, in a hospital setting, may provide the prescription to a nurse or other physician who may administer the prescription.

SUMMARY

In a first exemplary embodiment, the present disclosure is directed at a method for creating a prescription on a computer having a screen display. The method may therefore involve inputting at least a portion of medical prescription text into a single interface field on a screen display wherein the text is provided as continuous text and includes information regarding at least two of the following: medication name, dosage, route, frequency or quantity. The inputted text may be parsed and prompts and/or hints may also be provided for completing the medical prescription text as the text is input into the computer. The method may also validate the medical prescription text with respect to at least one of the dosage, route, frequency or quantity. Such validation may be based upon existing patient information or based upon established protocols for a given/selected medication.

In another exemplary embodiment the present disclosure relates to an article comprising a storage medium having stored thereon instructions that when executed by a machine result in the following operations: receiving at least a portion of medical prescription text into a single interface field on a screen display wherein the text is provided as continuous text and includes information regarding at least two of the following: medication name, dosage, route, frequency or quantity; parsing the received portion of medical prescription text; providing prompts and/or hints for completing the medical prescription text as the text is input into the computer; and validating the medical prescription text with respect to at least one of the dosage, route, frequency or quantity.

In another exemplary embodiment the present disclosure relates to a system for processing orders from medical prescription text comprising a user interface capable of receiving at least a portion of medical prescription text into a single interface field on a screen display wherein the text may be provided as continuous text and includes information regarding at least two of the following: medication name, dosage, route, frequency or quantity. A processor may then be supplied that is capable of communicating with the user interface and parsing the received portion of medical prescription text. The processor may also be configured to access at least one database and provide auto-completion prompts and/or hints from the database to the user interface for completing the medical prescription text. The processor may also be configured to validate the medical prescription text by comparing the medical prescription text with information from at least one selected database, which database may include patient and/or medication (drug) information.

BRIEF DESCRIPTION OF DRAWINGS

The above-mentioned and other features and advantages disclosed herein, and the manner of attaining them, will become more apparent and better understood by reference to the following description of embodiments taken in conjunction with the accompanying drawings, wherein:

FIG. 2 illustrates one example of a graphical user interface and the associated feature of a text box that allows for entry of medical prescription text analogous to a written prescription.

FIG. 6 illustrates patterns defined in XML.

FIG. 7 illustrates the entry of prescription text information in the indicated text field and the database reaction to such entry.

FIG. 9 illustrates a database table that may be used to track user-specific information.

DETAILED DESCRIPTION

As noted above, the present disclosure relates to a system, apparatus and method for the automated interpretation of medical prescription text. Medical prescription text may include information regarding a given prescription, which may therefore include medication name (e.g. generic or trade name), dosage (e.g. weight or volume), route (e.g. by mouth or orally, topical, etc.), frequency (e.g. number of dosages over a given time) and/or quantity (e.g. number of dosages in total). As noted, such text may be analogous to that which a physician may enter in a written prescription format, i.e. the text may continuously flow with a sequence of terms with any one or more of the above noted specified prescription parameters. Accordingly, continuous text herein may be understood as text that may be introduced into a single graphic user interface field location (e.g. an Rx input text box) that may receive at least two of such parameters, e.g., medication name and dosage, medication name and route, route and frequency, quantity and frequency, quantity and dosage, medication name and quantity, etc. In addition, such parameters may be spaced, punctuated or otherwise hyphenated. Furthermore, automated interpretation may be understood as interpretation by one or more of the programs associated herein with the disclosed system or apparatus.

Figure 1:
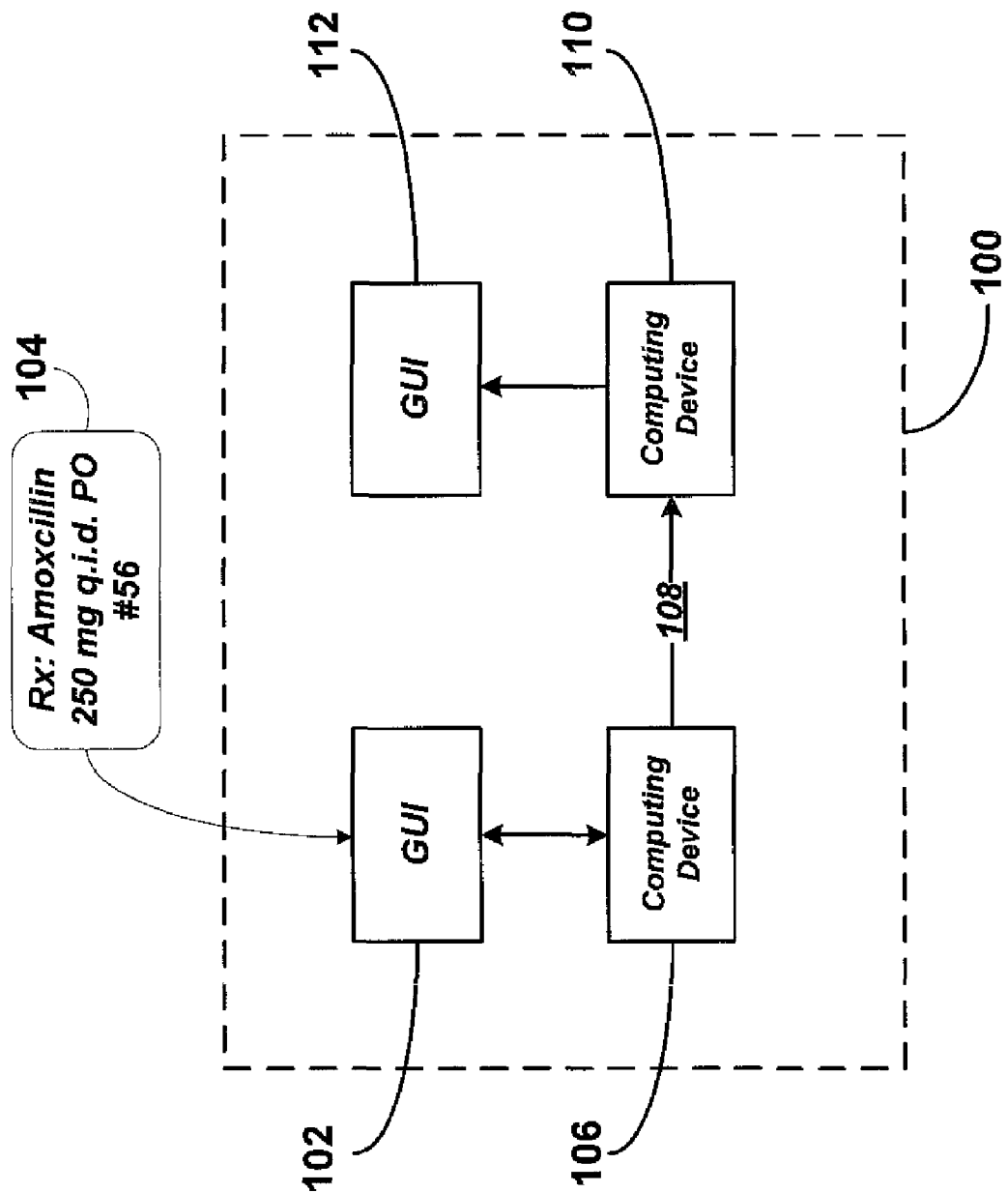
FIG. 1 is an exemplary overview of the system herein which is capable of receiving medical prescription text via a user interface.

FIG. 1 illustrates in general format an example of a system 100 wherein a user interface 102 is capable of receiving medical prescription text 104 for a selected patient. The user interface may include a graphical user interface displayed on a screen or touch screen where the provider may enter information using a keyboard, mouse, etc. In addition, the user interface may also include a handheld or wireless type device capable of remotely accessing the system. The medical prescription text may be input to the system by a medical practitioner/provider, such as a physician, therapist, nurse, etc. As noted above, the text may be entered in the format of written prescription text so that the provider is capable of entering prescription information in the manner that they may be accustomed as opposed to entry of information into multiple and discrete selected fields. As may be appreciated, such field entry type systems may be considered relatively time-consuming and relatively inefficient compared to a given practitioner's accustomed manner of issuing and drafting prescription type information.

The text 104 may then be immediately parsed or otherwise analyzed using one or more computing devices 106. That is, the medical prescription text may be parsed and checked for validity. With respect to such validity, the prescription may be checked with regards to a given patient, such as whether or not other medications are currently be administered to a given patient. This may then provide warnings to the provider when problems are identified. For example, a database may be provided that would identify problems associated with potentially adverse drug interactions. This may include an identification of drug allergies due to prior patient contact with a given drug and/or a potentially adverse reaction that may take place in view of a pre-existing medication program of a given individual. Validation may also be non-patient specific, e.g. warnings may be supplied regarding idiosyncratic reactions due to unexpected or peculiar reactions that may occur in a relatively small percentage of individuals. In addition, validation may consider whether the input information regarding the particular medication, dosage, routing, frequency and/or quantity is consistent with established protocols for such drug administration.

The medical prescription text may then be "signed" by the provider or otherwise verified/authenticated and forwarded to an entity or appropriate individual to execute/dispense the prescription order. Accordingly, the medical prescription may be received by an executing party at the user interface 102 where the initial prescription was entered and/or communicated over a network 108 to another computing device 110 and supplied on another user interface 112. The prescription may then be formulated and ultimately delivered to the patient.

As noted above, the system or apparatus may include a graphical user interface (GUI) and a parsing system that may allow for the integration of one or more databases, including patient information, available medications, medical terms and/or other information that may be incorporated into a database to assist in prescription selection. Thus, it may be appreciated that changes to databases and associated look-up tables (LUT) may occur on a regular basis and/or at random intervals depending upon the importance of the information relative to a given prescription drug therapy protocol.

Figure 2:
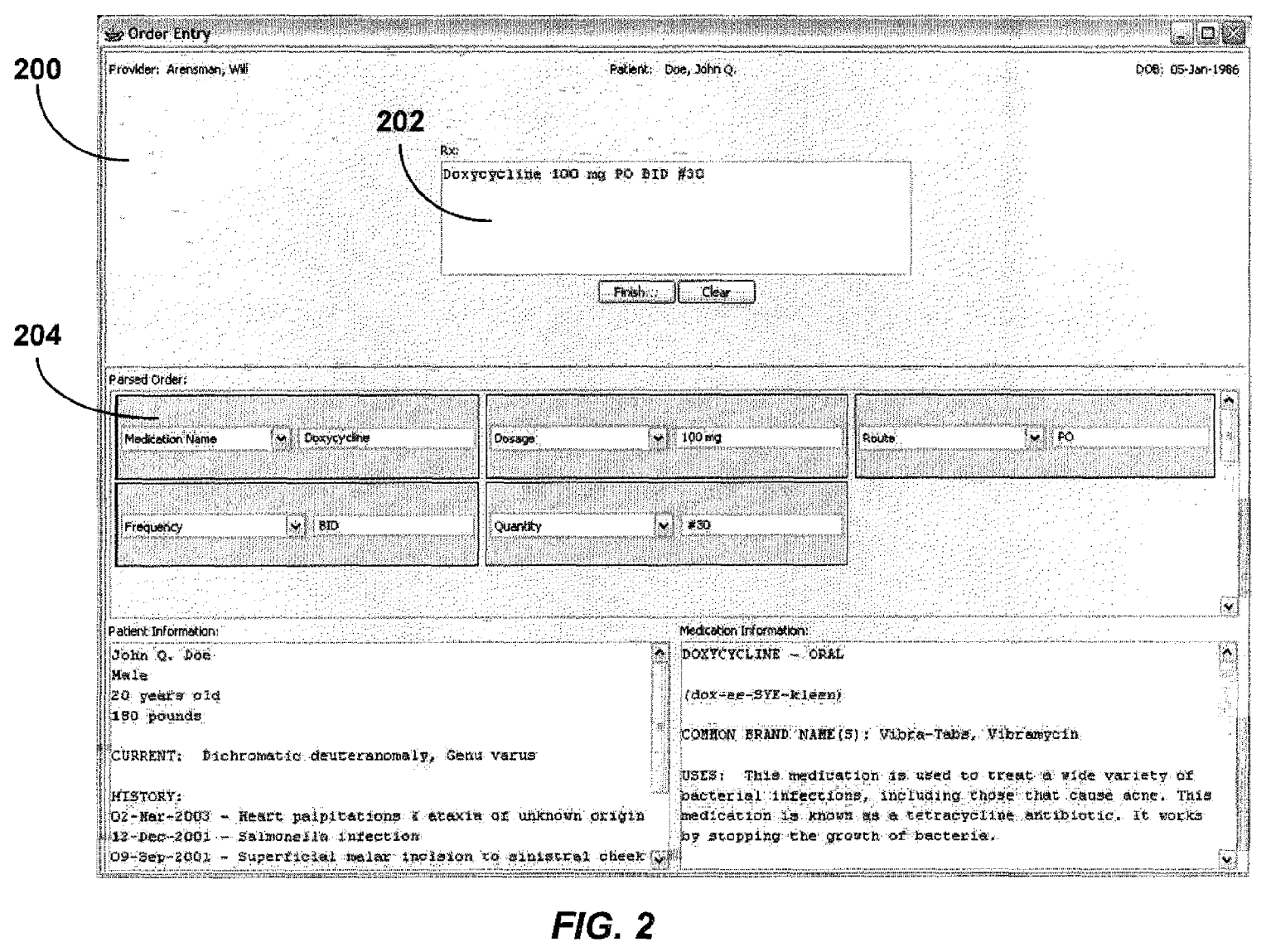

FIG. 2 illustrates in more relative detail an exemplary graphical user interface 200 which may allow for the provider to enter information into a text box 202 which may be understood herein as a single field location. The information may include the medical prescription text noted above. Again, where the medical prescription text may be a prescription for medication, the provider may enter a medication name, dosage, means of delivery, number of units to dispense, etc. As discussed further below, the text box may be capable of providing auto-completion of the text being entered and supply the provider with hints. The interface may also identify one or more additional interface fields 204 (i.e. separate from and in addition to text box 202). These fields 204 may represent the medical prescription text, the dosage, the route, the frequency and/or the quantity as parsed and recognized by the computing device. Where insufficient information has been entered, the fields may separately act as prompts for the provider to complete the medical prescription text. For example, once a medication name has been entered, the dosage, route, frequency and quantity fields may appear to prompt entry of such information in the text box 202. Where the text may be incorrectly parsed, the information entered in the fields may be altered by the provider to correct the parsed information. In addition, to provide additional hints, the fields may themselves include drop down boxes for correcting the parsed information.

Furthermore, the graphical user interface may provide other widgets, i.e., other graphical elements may be included to interact with the program and various databases in which information may be stored. The graphical user interface may be designed with a number of programs, such as Swing, which may be understood as a graphical user interface toolkit for Java. However, it should be appreciated that other programs may be utilized herein.

Figure 3:
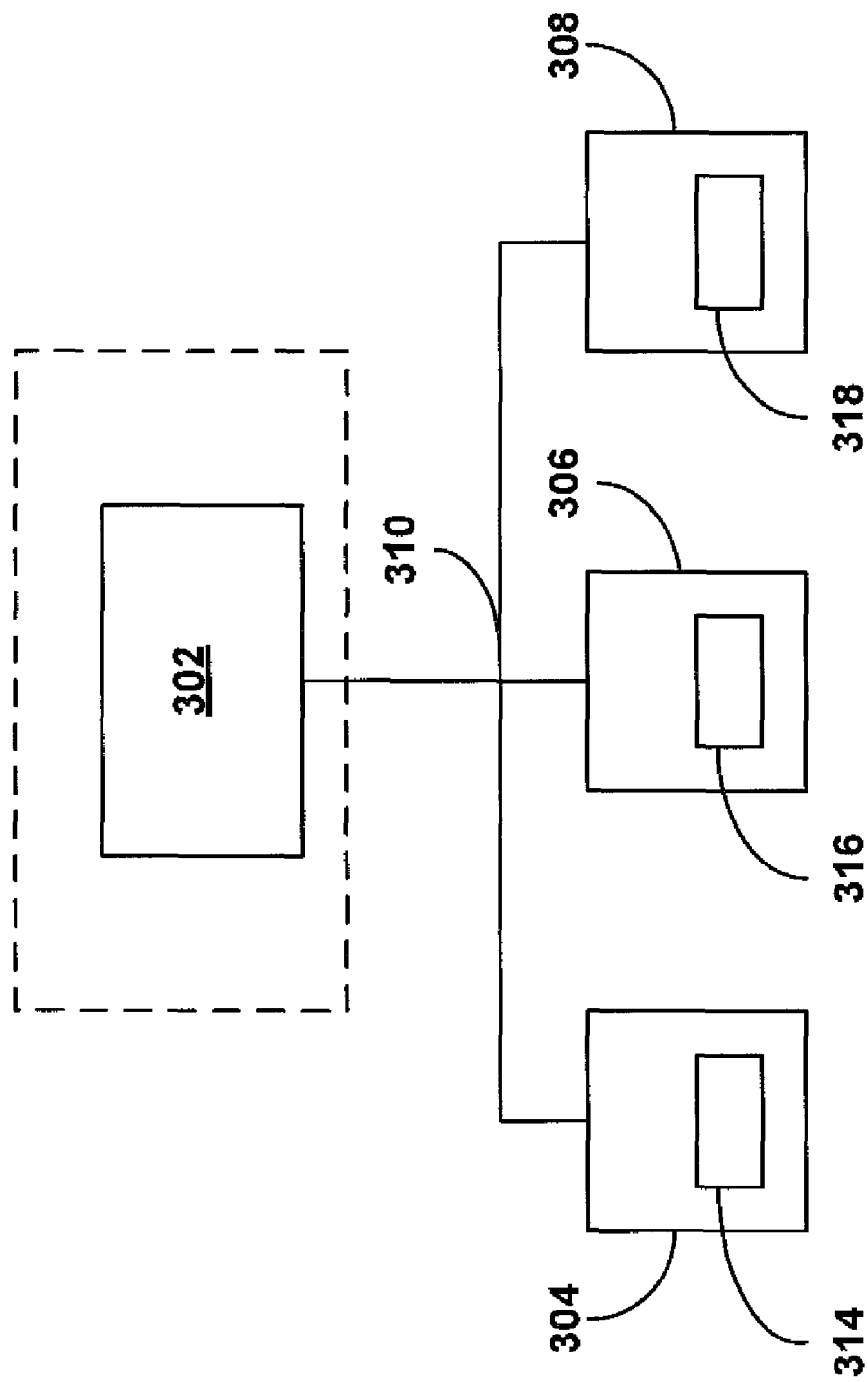
FIG. 3 illustrates the general system requirements supporting the parsing and analysis of the medical prescription text.

Turning to FIG. 3, parsing may be performed by a processor 302 within the computing device 106 (illustrated in FIG. 1), which may analyze the medical text information entered by a provider. The processor 302 may access a number of databases 304, 306, 308 to facilitate parsing of the entered information. These databases 304, 306, 308 may be located within the computing device 106, or may be located in other locations and made available over a network 310, as illustrated. An example of a database may include an Oracle Database. The databases may include one or more look-up tables 312, 314, 316 stored in memory. In addition, the information in the look-up tables may be changed as the information regarding patients, medical terms, medication information, diagnostic tests and laboratory screenings change. Thus, changes to the databases and look-up tables may occur on a regular basis or at random intervals depending on, for example, the importance of the changes in information.

With respect to parsing (transformation of the input text into a data structure for analysis) it may be understood herein that the medical prescription text that is entered by the provider may be separated into various components or tokens. Accordingly, in a general sense, and with respect to written prescription text, parsing herein may involve transformation of the entered information into segments representing the medication name, dosage, route, frequency and/or quantity.

Furthermore, parsing may accommodate the written prescription text as a natural human language, and may be regarded as a form of natural language processing. Accordingly, with respect to written prescription text, parsing may accommodate the irregularity and informal nature of natural language. For example, while one provider may enter the written prescription entry, Doxycycline 100 mg BID PO #30, another provider may enter an equivalent prescription, Doxycycline 100 mg sig: T 1 tab PO BID disp: 30 tabs. In addition, parsing may be extensible and accommodate prescribing habits that were not initially accounted for in the design of the parsing system. The extension of the parsing system may be accomplished through interaction with the user rather than fundamental changes to parsing implementation.

Parsing herein may also be performed with each keystroke. As the provider enters each additional character of the prescription text, feedback regarding the status of parsing may be provided indicating how text segments have been classified. As may be appreciated, parsing in this fashion differs from parsing systems that rely on complete text entries and only provide feedback when the user indicates text entry is complete.

Parsing herein may be specifically implemented by using context free grammar defined in extensible markup language (XML). As may be appreciated, XML allows the system herein to define its own programming tags and may also provide sharing of the data across different information systems via the Internet.

Figure 4:
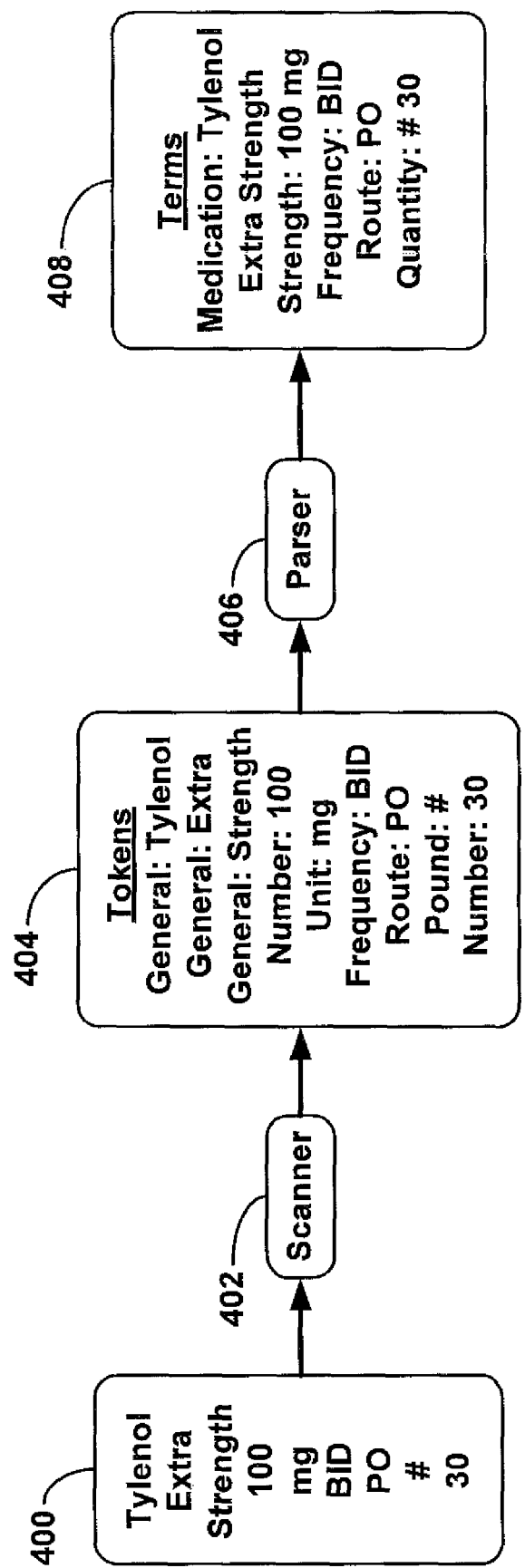
FIG. 4 provides one illustration of provider input into a graphical user interface (GUI).

FIG. 4 illustrates yet another example of provider input 400 into a GUI. In this particular example the provider may input the following, which as noted, may be recognized as that type of information that is analogous to a written prescription entry: Tylenol Extra Strength 100 mg BID PO #30. Turning then to consideration of the processing that may take place herein, the text may now be scanned at 402 and broken into tokens at 404, wherein breaks, such as tabs or spaces may indicate new tokens. The tokens may then be characterized and parsed 406 into a number of categories, such as general text, numbers, units, frequency, route of delivery, amount to dispense, etc. General text (Tylenol Extra Strength) may be interpreted as medication names. As may be appreciated, the system herein may be configured to recognize trade names and/or generic names of a given drug. Strength may be indicated by units of measurement such as mg, g, gr., ml, inch, oz., ounces, gm, cc, units, grams, etc. Dose measurements may be indicated by phrases such as tab, tabs, puffs, gtt, g++, glass, tube, jet, appl, tsp, bottle, etc. Frequencies may be identified by phrases such as BID, daily, PRN, TID, QAM, QPM, @, ONSET, REPEAT, IN AM, QDX, etc. Total number of doses may be identified by phrases such as #, No., Qt. or Qty. Each of these terms or phrases may be referenced and compared to those stored in a database, as illustrated above in FIG. 3.

Accordingly, it may now be appreciated that numbers associated with units of measure may be parsed on placement. For example, if a number is placed before a phrase indicating a unit of measure it may be associated with such unit of measure. In the above example the number "100" was placed before the term "mg" and the system therefore parses and recognizes that the prescription strength is "100 mg." On the other hand, if a number is placed after a phrase such as # the system may therefore parse and recognize this as the quantity or total number of dosages.

Figure 5:
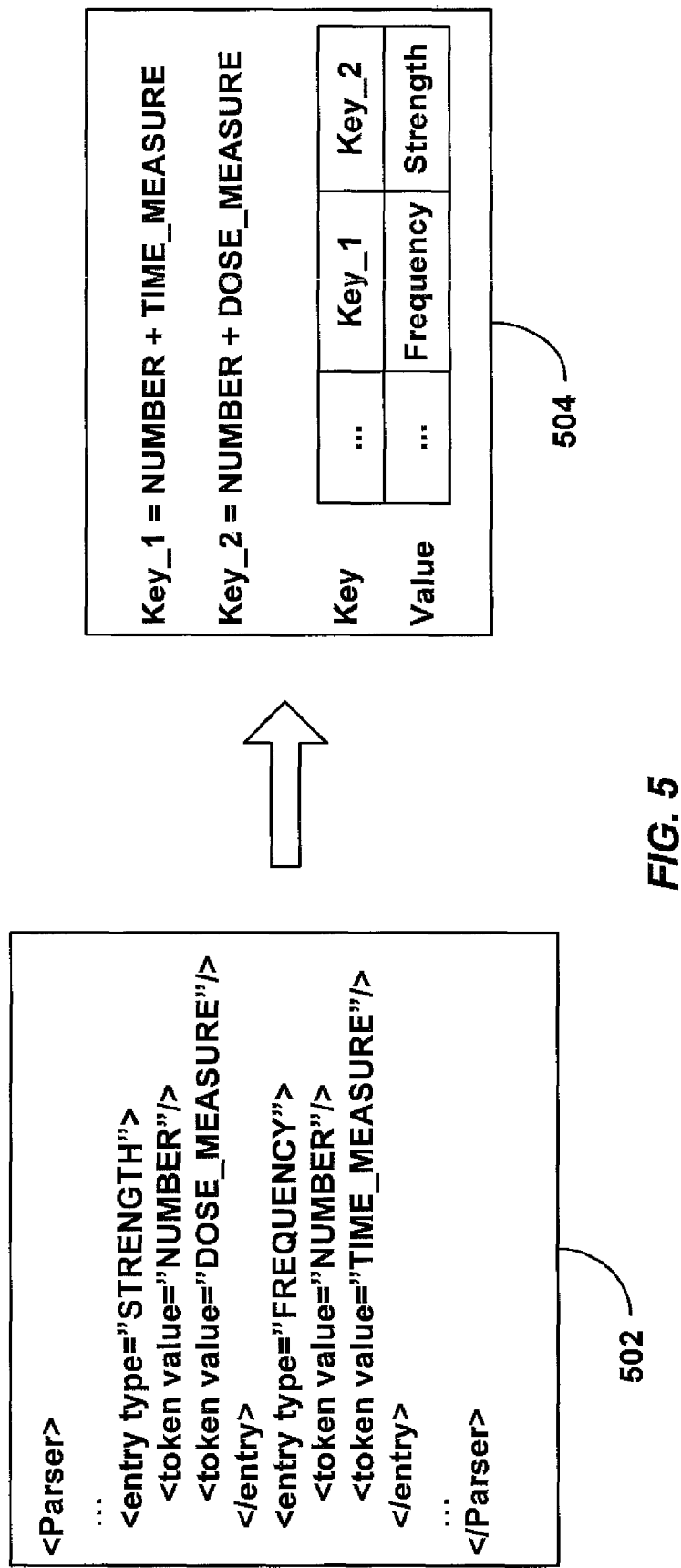
FIG. 5 illustrates an exemplary parser definition file and parser at runtime.

The parsing system or software may therefore include parsing algorithms, which may be defined by a number of parser definitions. These definitions may be used to crease a parser at runtime (inputting of prescription text information). FIG. 5 illustrates an exemplary parser definition file 502 and parser at runtime 504. The content parsed in the figure is an exemplary prescription. However, it should be appreciated that the content parsed may be any and all of the prescription text discussed herein.

Prompts and hints may also be given to the provider. For example, when a provider initiates the prescription text with a strength measurement, the dose form and medication name will typically follow. Thus, utilizing pattern recognition, an auto-completion system may use this information to determine that a medication name may be a relevant prompt to supply to the provider, when strength and dosage have been identified. Such prompts may be supplied on the graphical user interface. FIG. 6 illustrates how the patterns may be defined in XML. In addition, the pattern recognition may be associated with a specific provider or patient.

Figure 7:
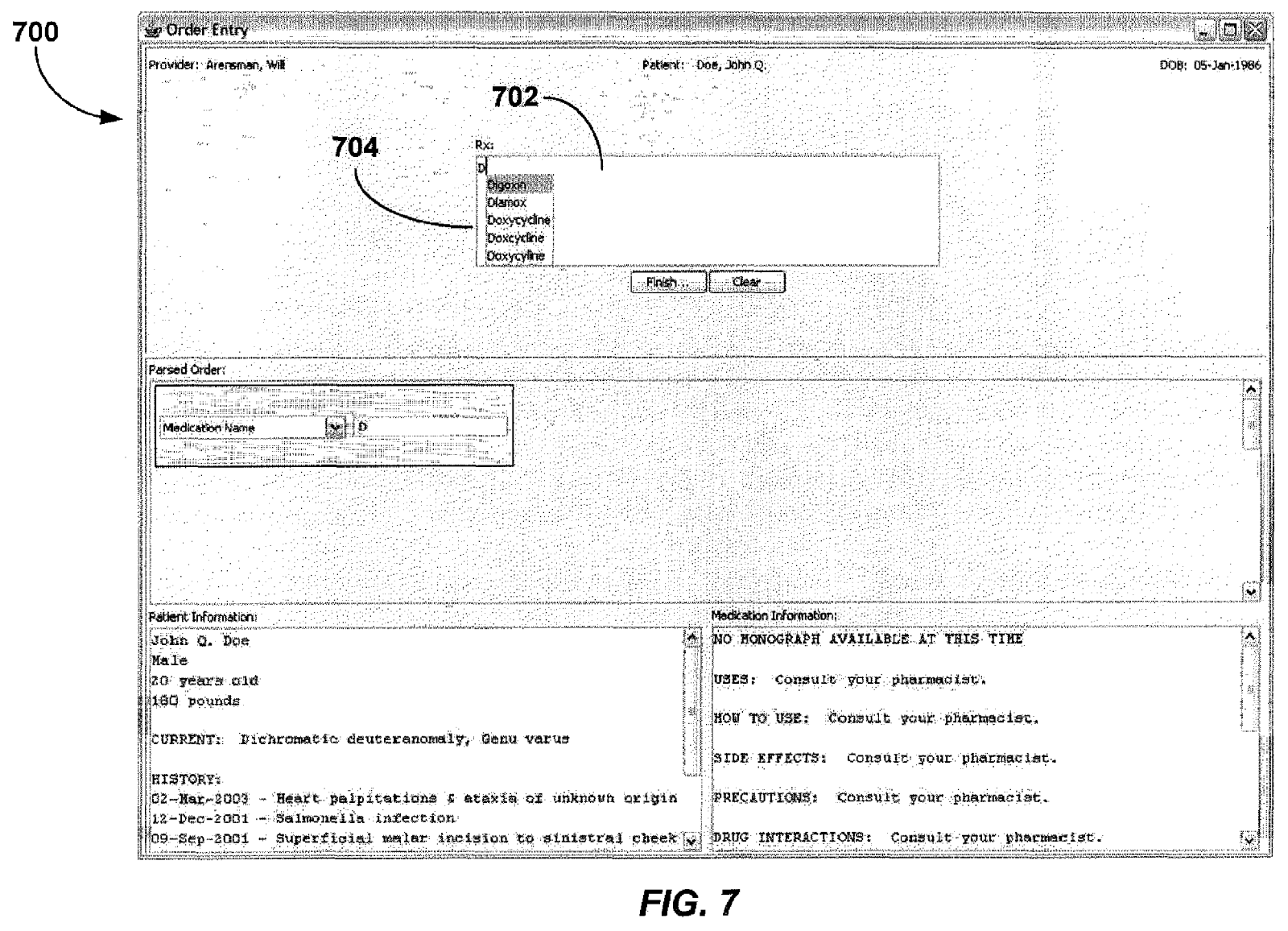

FIG. 7 illustrates a medication name being entered into the text field 702 of the graphical user interface (GUI) 700. As the provider enters the individual letters, in this case the letter "D", a database may be referenced for all medications beginning with the letter "D" and provide a list 704, such as a drop down list, arranged in alphabetical order of corresponding medication names to the provider. As the provider continues to enter letters into the GUI, the database may be referenced for all medications with the additional entered letters. Thus, for example, where the provider is requesting the antibiotic "Doxycycline" and types the combination "Do", terms like "Digoxin" may be removed from the list of corresponding medication names.

As text is entered each input (including individual key strokes) may be checked, as noted above, for validity. For example, when entering a prescription for a medication, once the dosage is indicated, reference may be made to appropriate dosages for the specific medication in a look-up table. If the dosage information is present and matches that in a database, an indication may be provided that the information is correct and valid. If the information is not present or does not match the database, another indication may be provided warning that the information is incorrect or invalid. Further processing may provide information as to whether the prescribed procedure or medication may be available, in-stock at a given location, as well as compatible or incompatible with other prescriptions that the patient may be taking.

The indication of validity may be made visually or even by sound. For example, the fields may turn green, a check may appear in the screen, or a dialog box may indicate validity, etc. Once the medical text information has been recognized, parsed and validated, the provider may complete the order by pressing a "finish" button which may indicate that the medical prescription text may then be supplied or forwarded to one who executes the order.

Accordingly, one may appreciate that the above may be executed by one or more threading algorithms, which may be capable of executing the various tasks, i.e., receiving the input, parsing the input and providing feedback in the form of prompts and hints. Threads or threads of execution may be understood as a mechanism for allowing a program to divide itself into two or more simultaneous running tasks. Simultaneous execution may be either truly simultaneous, by providing more than one processor core for each thread, or may appear simultaneous even though a processor may switch back and forth between multiple tasks.

Figure 8:
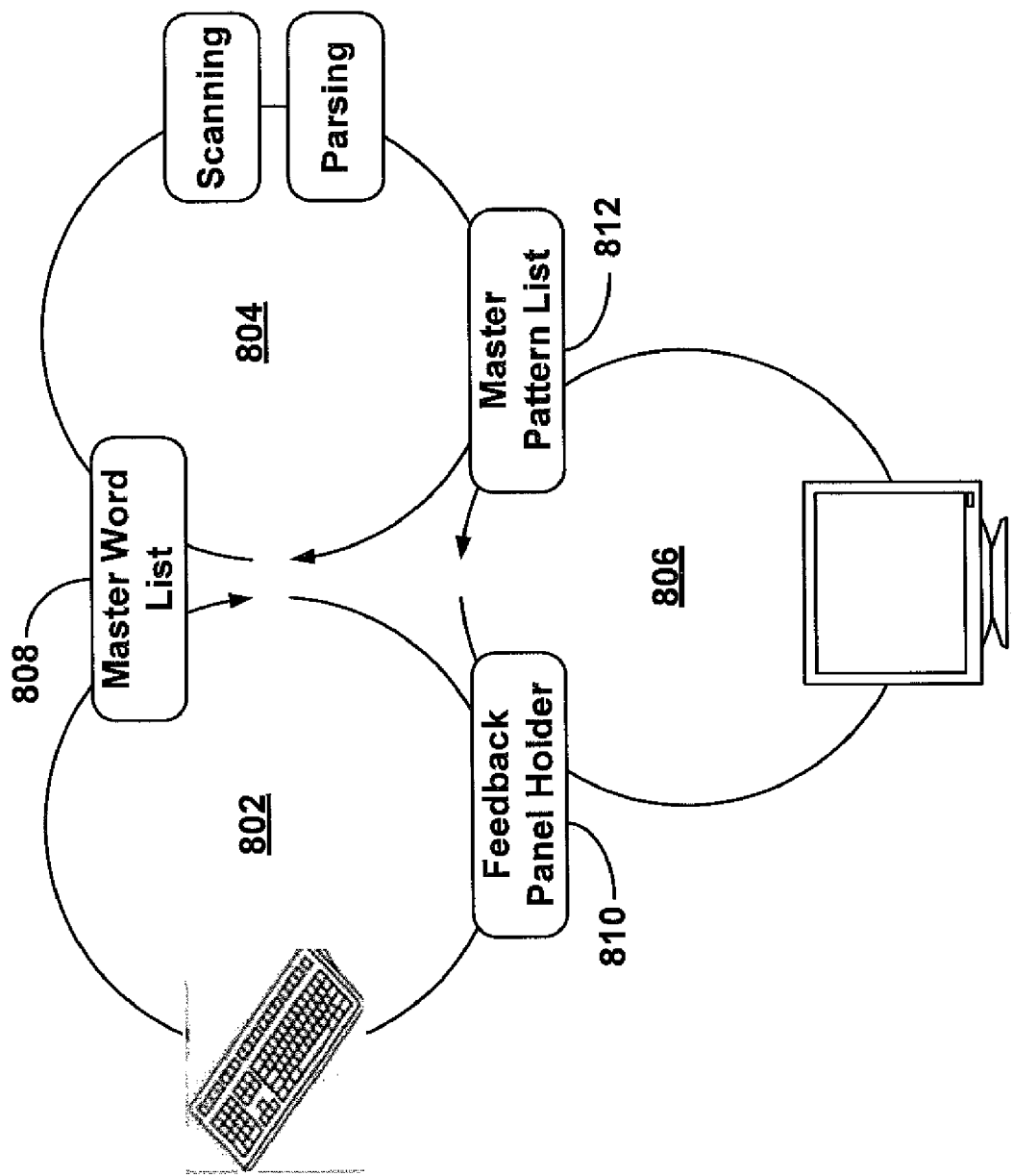
FIG. 8 illustrates the threading capability of the present system.

An example of how the threading algorithms may interact is illustrated in FIG. 8, which depicts three threads 802, 804, 806 working in concert. The first thread 802 includes an input thread, wherein each keystroke may be receiving and analyzed. This thread may obtain an exclusive lock on a master word list 808, which may be used to synchronize the threads. It can be noted that one specific example of a master word list was provided above by way of item 400 in FIG. 4. In addition, this thread may place text into a master word list. The second thread 804 may be a parsing thread which parses each entered keystroke. As noted above, the parsing thread may apply a scanner and parser to the text and may access a database if necessary. The final thread 806 may be a feedback thread, which may place the GUI configuration in the feedback panel holder, which in turn may be offered to the provider through the GUI as the provider types the medical prescription text into the text box field.

With attention back to FIG. 2, it may now also be appreciated that the system herein may also maintain the text field 202 synchronized with the individual fields 204. Accordingly, if a provider elects to change any one or more of the medication name, dosage route, frequency or quantity in the text field 202, the system automatically will synchronize such change in the individual fields 204. In addition, if a provider elects to change any one or more of the such inputs in the individual fields 204, the system may again automatically synchronize such change in the text field 202.

In addition to the above, the system may also be configured such that it may be modified in its operation with use. That is, the system may ultimately tailor the prompts and hints returned to a provider based on information characteristic of a given provider, the patient, the facility location (e.g. available medications at a given facility), etc. For example, the system may recognize through a pattern of use that the particular provider repeatedly selects certain medications in a text field (e.g. those starting with a given letter) more so than other medications that may be available in such field. That being the case, when prompts are supplied, the medications that have been historically selected by such provider may be initially listed over those medications that may nonetheless be available in such field. In addition, the system may also recognize that for a given historically popular medication in a given text field, such medication may be selected at a regular treatment level (e.g. at a given dosage level and frequency) and the system may therefore prompt such levels as soon as the provider enters a particular term. For example, when the terms "mg" and/or "Br" are entered, the system may follow with, e.g., the numerical level of "100" and the letter "D" which may then track the historical treatment level of 100 mg BID selected by the provider for the identified medication.

With attention directed to FIG. 9, a database table may be supplied that tracks user-specific information. In this situation, the system may provide auto-completion prompts that are based upon a particular user so that the practitioner may be provided with historical treatment protocol information that is patient specific. For example, with respect to FIG. 9, a listing may be compiled of the various particular medications supplied to a given patient. In such a situation, when the provider inputs, e.g., "PRE" the auto-completion may next propose "PREDNISONE" as a possible medication based upon the fact that "PREDNISONE" was a previous medication for this particular patient. As may therefore be appreciated, the system herein may provide auto-completion prompts upon entry of a given prescription based upon a patient's previous medications, dosage levels, frequency of administration, route and/or quantity.

In addition, the system herein may tailor the prompts to a provider based upon individual patient characteristics, such as weight and age. For example, should a patient be underweight relative to general statistical norms, the system may identify from an appropriate look-up table the characteristic dosage for such weight group and prompt the provider accordingly for a given medication. Similarly, the system may consider the age of a patient and again, from an appropriate look-up table that may take into account age of a patient for a particular medication, offer the appropriate prompts that are characteristic of a given prescription dosage for a given age demographic.

Figure 10:
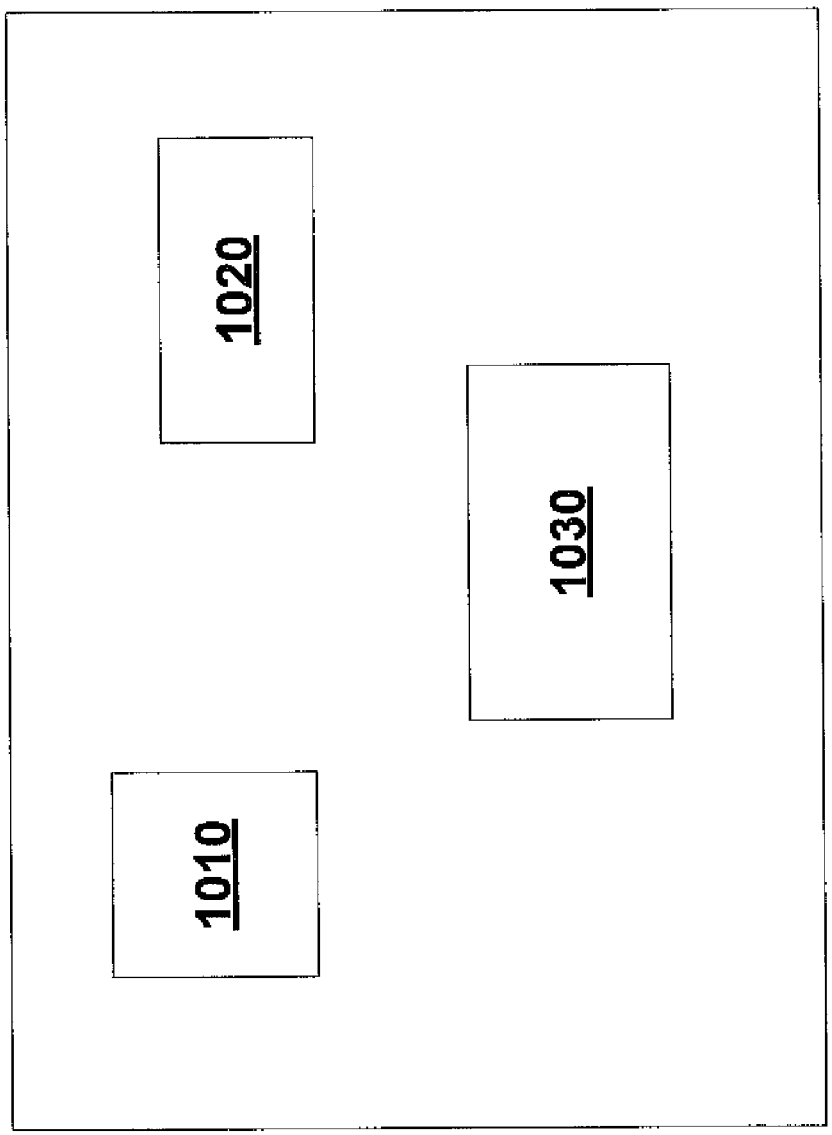
FIG. 10 illustrates a processor, machine readable media and a user interface that may be used herein to implement the automated interpretation of medical prescription text.

It should be noted that the functionality herein for the embodiments in the present disclosure may be implemented using hardware, software, or a combination of hardware and software, either within a system completed herein or in communication with the system here, as may be desired. If implemented by software, as noted, a processor and machine readable memory may be utilized. The processor may be any type of processor capable of providing the speed and functionality required by the embodiments of the present disclosure. Machine-readable memory includes any media capable of storing instructions adapted to be executed by a processor. Some examples of such memory include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk, (e.g. CD-ROM), and any other device that can store digital information. The instructions can be stored on medium either in a compressed or encrypted format. Accordingly, in the broad context of the present disclosure, and with attention to FIG. 10, the system may contain a processor (1010), machine readable media (1020) and user interface (1030).

The foregoing description of several methods and an embodiment(s) has been presented herein for purposes of illustration. It is not intended to be exhaustive or to limit the disclosure to the precise steps and/or forms disclosed, and many modifications and variations are possible in light of the above teachings. It is intended that the scope of the invention be defined by the claims appended hereto.

What is claimed is:

1. A method for creating a prescription on a computer having a screen display comprising:
   inputting at least a portion of medical prescription text for a medication into a single interface field on said screen display wherein said text is provided as continuous text and includes information regarding at least two of the following: medication name, dosage, route, frequency or quantity;
   parsing the received portion of medical prescription text;
   providing prompts and/or hints for completing the medical prescription text as said text is input into said computer;
   providing an additional interface field for each of a medication name, dosage, route, frequency and quantity on said screen display subsequent to parsing of said medical prescription text in said single interface field, wherein each field separately acts as a prompt to complete the medical prescription text and to correct the parsing of the medical prescription text;
   validating the medical prescription text with respect to at least one of the dosage, route, frequency or quantity, wherein validating said medical prescription text comprises comparing said medical prescription text with at least one of information stored in a database regarding a patient and information stored in a database regarding said medication; and
   providing a warning if the medical prescription text does not match information stored in the database regarding the patient or the information stored in the database regarding said medication.

2. The method of claim 1 wherein said single interface field comprises a single input text box on a graphical user interface.

3. The method of claim 1 wherein said continuous text includes information comprising at least three of the following: medication name, dosage, route, frequency or quantity.

4. The method of claim 1 wherein said continuous text includes information comprising at least four of the following: medication name, dosage, route, frequency or quantity.

5. The method of claim 1 wherein said continuous text includes information comprising the following: medication name, dosage, route, frequency and quantity.

6. The method of claim 1, wherein parsing the received portion of medical prescription text is performed by scanning said medical prescription text, configuring said medical prescription text into tokens, characterizing said tokens and parsing said medical prescription text.

7. The method of claim 1 wherein said prescription text comprises a plurality of characters and said parsing the received portion of the medical prescription text takes place upon inputting of each character of said prescription text.

8. The method of claim 1, wherein providing prompts comprises providing fields for additional medical prescription text.

9. The method of claim 1, wherein providing hints comprises providing drop down or auto-completion text.

10. An article comprising a storage medium having stored thereon instructions that when executed by a machine result in the following operations:
  receiving at least a portion of medical prescription text for a medication into a single interface field on a screen display wherein said text is provided as continuous text and includes information regarding at least two of the following: medication name, dosage, route, frequency or quantity;
  parsing the received portion of medical prescription text;
  providing prompts and/or hints for completing the medical prescription text as said text is input into said computer;
  providing an additional interface field for each of a medication name, dosage, route, frequency or quantity on said screen display subsequent to parsing of said medical prescription text in said single interface field, wherein each field separately acts as a prompt to complete the medical prescription text and to correct the parsing of the medical prescription text;
  validating the medical prescription text with respect to at least one of the dosage, route, frequency or quantity, wherein validating said medical prescription text comprises comparing said medical prescription text with at least one of information stored in a database regarding a patient and information stored in a database regarding said medication; and
  providing a warning if the medical prescription text does not match information stored in the database regarding the patient or the information stored in the database regarding said medication.

11. The article of claim 10, wherein parsing the received portion of medical prescription text is performed by scanning said medical prescription text, configuring said medical prescription text into tokens, characterizing said tokens and parsing said medical prescription text.

12. The article of claim 10 wherein said prescription text comprises a plurality of characters and said parsing the received portion of the medical prescription text takes place upon inputting of each character of said prescription text.

13. A system for processing orders from medical prescription text comprising:
  a user interface capable of receiving at least a portion of medical prescription text for a medication into a single interface field on a screen display wherein said text is provided as continuous text and includes information regarding at least two of the following: medication name, dosage, route, frequency or quantity;
  a processor capable of communicating with said user interface and parsing the received portion of medical prescription text;
  said processor further capable of accessing at least one database and providing auto-completion prompts and/or hints from said database to said user interface for completing the medical prescription text;
  said processor further capable of providing an additional interface field for each of a medication name, dosage, route, frequency or quantity on said screen display subsequent to parsing of said medical prescription text in said single interface field, wherein each field separately acts as a prompt to complete the medical prescription text and to correct the parsing of the medical prescription text;
  said processor further capable of validating the medical prescription text by comparing said medical prescription text with information from at least one database, wherein validating said medical prescription text comprises comparing said medical prescription text with at least one of information stored in a database regarding a patient and information stored in a database regarding said medication; and
  said processor further capable of providing a warning if the medical prescription text does not match information stored in the database regarding the patient or the information stored in the database regarding said medication.

14. The system of claim 13 wherein said single interface field comprises a single input text box on a graphical user interface.

15. The system of claim 13, wherein said processor is capable of parsing the received portion of medical prescription text by scanning said medical prescription text, breaking said medical prescription text into tokens, characterizing said tokens and parsing said medical prescription text.

* * * * *